(12) United States Patent
Mortimer et al.

(10) Patent No.: US 10,175,125 B1
(45) Date of Patent: Jan. 8, 2019

(54) PLANAR SENSOR FOR SENSING LATERAL DISPLACEMENT AND SHEAR

(71) Applicants: Bruce J. P. Mortimer, Casselberry, FL (US); Gary A. Zets, Casselberry, FL (US)

(72) Inventors: Bruce J. P. Mortimer, Casselberry, FL (US); Gary A. Zets, Casselberry, FL (US)

( * ) Notice: Subject to any disclaimer, the term of this patent is extended or adjusted under 35 U.S.C. 154(b) by 0 days.

(21) Appl. No.: 15/019,470

(22) Filed: Feb. 9, 2016

Related U.S. Application Data

(60) Provisional application No. 62/113,753, filed on Feb. 9, 2015.

(51) Int. Cl.
| | |
|---|---|
| *G01L 1/12* | (2006.01) |
| *G01B 7/14* | (2006.01) |
| *G01L 5/00* | (2006.01) |
| *A61B 5/11* | (2006.01) |
| *A61B 5/103* | (2006.01) |

(52) U.S. Cl.
CPC ............ *G01L 1/127* (2013.01); *A61B 5/1038* (2013.01); *A61B 5/112* (2013.01); *G01B 7/14* (2013.01); *G01L 5/00* (2013.01)

(58) Field of Classification Search
CPC ... G01L 1/27; G01L 5/00; G01L 1/127; G01L 1/122; G01L 1/125; A61B 5/1038; A61B 5/112; G01B 7/14; G01G 3/16
USPC .......................................................... 73/779
See application file for complete search history.

(56) References Cited

U.S. PATENT DOCUMENTS

| | | | | |
|---|---|---|---|---|
| 4,777,824 A | * | 10/1988 | Alers ......................... | B06B 1/04 324/226 |
| 5,081,870 A | * | 1/1992 | Fitzgerald ................ | G01N 3/38 73/575 |
| 5,287,056 A | * | 2/1994 | Jackson .................. | G01R 33/14 324/212 |
| 6,642,711 B2 | * | 11/2003 | Kawate ................... | G01B 7/003 324/207.17 |
| 7,250,763 B2 | * | 7/2007 | Mikhaltsevitch .... | G01R 33/441 324/318 |
| 7,571,697 B2 | * | 8/2009 | Benjamin .............. | H01J 37/321 118/723 I |
| 8,925,385 B2 | * | 1/2015 | Korpi ........................ | G01G 3/16 73/19.03 |
| 8,966,991 B2 | * | 3/2015 | Ullakko ................... | G01L 1/127 73/777 |
| 2015/0362340 A1 | * | 12/2015 | Montagne .............. | G01D 5/225 324/207.17 |

* cited by examiner

*Primary Examiner* — Jonathan Dunlap
*Assistant Examiner* — Octavia Hollington
(74) *Attorney, Agent, or Firm* — Larry D. Johnson

(57) ABSTRACT

A planar sensor for sensing lateral displacement and shear measures the displacement of a small ferromagnetic or diamagnetic target that is positioned and allowed to move laterally over a series of specially shaped and orientated planar coils. The coils are preferably multi-layer printed circuit boards (PCB) that contain the planar windings and in other embodiments can be fabricated using flexible PCBs or using micro electromechanical (MEMS) assemblies. The target displacement is constrained to a general area and in multiple lateral directions (measuring shear).

20 Claims, 14 Drawing Sheets

PLANAR SENSOR FOR SENSING LATERAL DISPLACEMENT AND SHEAR

CROSS REFERENCE TO RELATED APPLICATIONS

The present application claims the benefit of the filing date of U.S. Provisional Patent Application Ser. No. 62/113,753, filed Feb. 9, 2015. The foregoing application is incorporated by reference in its entirety as if fully set forth herein.

STATEMENT REGARDING FEDERALLY SPONSORED RESEARCH OR DEVELOPMENT

Developed under DHP-12-008, Multisegmental Sensor Integration for Balance Control, Contract Number W81WH-13-C-0129.

REFERENCE TO A MICROFICHE APPENDIX

Not applicable.

TECHNICAL FIELD

The present invention relates generally to sensors and associated apparatus, and more specifically to an improved sensor apparatus for sensing lateral displacement and shear.

BACKGROUND INFORMATION AND DISCUSSION OF RELATED ART

Shear stress is defined as the component of stress that is coplanar with a material cross section. Shear stress arises from the force vector component parallel to the cross section and is defined as force applied divided by the cross sectional area of the deformed material with area parallel to the applied force. The applied force is often referred to as the shear, or lateral force.

There is a large class of sensing applications that require the measurement of lateral displacements or forces. Ideally, these measurements should be with a small planar sensor that is robust and capable of measuring the lateral displacements or forces while simultaneously withstanding vertical loading. It is also desirable to have minimal cross coupling between the desired lateral force measurement and loading in the vertical direction. In certain applications it is also desirable to simultaneously measure the lateral and vertical forces.

A particularly interesting practical application for a planar lateral load sensor is in wearable motion capture. Human movement is the result of complex inter-dependent components that include joints, skeletal, neuro and muscular components. The study of human movement kinematics is usually undertaken by motion capture (mocap) sensor systems. Motion tracking technology is routinely used in biomechanical research, sports training, medical assessment, digital animation, virtual reality and computer/gaming interfaces to capture user biomechanical movements. Mocap systems are usually based on optical tracking, magnetic tracking, inertial sensors, ground-reaction force measurement, or combinations of these sensors (W Tao, T Liu, R Zheng and H Feng, Review: Gait Analysis Using Wearable Sensors, Sensors 2012, 12, 2255-2283).

Ground reaction force (GRF) is a vector that is the result of contact and can be measured using instrumented force-plates. The center of pressure (COP) is a related measure corresponding to the point of application of the ground reaction force vector. Analysis of COP is common in studies on human postural control and gait. It is thought that changes in motor control may be reflected in changes in the COP.

COP can be measured using instrumented mats (for example, Gait Mat II) and in instrumented shoes (for example, M3D, Xsens (ForceShoe), Pressure Profile (3D TruCapture) and TekScan (F-Scan VersaTek Wireless)). COP measured within an instrumented shoe will be specific to the associated limb; usually the COP for the left and right foot will be separately measured (together with the weight or load for each foot). If there is simultaneous weight on both shoes (i.e. the user has both feet in contact with the ground for example when standing or during aspects of gait), the COP of the user can then only be estimated by using the COP measured for each shoe and also an estimate of the location of the shoes.

Ground reaction force can be approximated by pressure or determined from the combination of pressure and shear using standard biomechanical models (D. Lafond, M. Duarte, F. Prince, Comparison of three methods to estimate the center of mass during balance assessment, Journal of Biomechanics 37 (2004) 1421-1426). Combination sensor systems have been proposed (for example by Xsens and ShapeWrap 3), which include six degrees of freedom force and moment sensors and miniature inertial sensors to estimate joint moments and powers of the ankle (Martin Schepers, Ambulatory Assessment of Human Body Kinematics and Kinetics, Thesis University of Twente, 2009). The combination of 3D motion sensors and GRF sensors in shoes has also been proposed as a clinic gait analysis human assistance tool.

Foot pressure (load) sensor designs based on capacitive (M Cheng et al. A Polymer-Based Capacitive Sensing Array for Normal and Shear Force Measurement, Sensors 2010 (10) 10211-10225), optical and piezoelectric sensors have been proposed but do not usually provide measurements of shear. Studies have shown (Kuo, A D. (1998)) a least squares estimation approach to improving the precision of inverse dynamics computations (J Biomech Eng 120:148-159). COP information may be sufficient to estimate shear forces using a least squares inverse dynamics (LSID) approach. However, this is computationally intensive (i.e. prone to delay) as the complete model must be known. Innovative instrumented shoes measure the shear directly using multi-axis load cells under the shoe (H. M. Schepers, et al. 'The Forceshoe': What Has Been Achieved?—Ambulatory Estimation of Ankle and Foot Dynamics and Center of Mass Movement. The 10th International Symposium on 3D Analysis of Human Movement, Oct. 28-31, 2008). However, this design is bulky, adds significant height to the shoe platform, and restricts the user to wearing specially designed and instrumented shoe.

There is an unmet need for an instrumented shoe that fits an insole form factor i.e. flexible and less than 5 mm thickness. This invention describes a sensor and approach for measuring lateral (shear) and vertical loads in a planar form factor that can fit within an instrumented insole in a shoe or in other locations, such as between layers of protective clothing, between clothing and the skin, between a held object and the hand, and others.

There are significant advantages to measuring in-shoe COP and loading (weight); the state classifier and process for discriminating between sitting, standing and walking activities is relatively simple, and the instrumented insole sensor can be potentially used to determine the ground reaction force and together with other segment data, the stability margin. Further, shear measurement (together with COP) is also a natural and rapid indicator of the various gait cycles including initiation and termination of gait. Shear is also a potentially sensitive measure of the onset of slip (and potential balance instability).

The foregoing information reflects the current state of the art of which the present inventor is aware. Reference to, and discussion of, this information is intended to aid in discharging Applicant's acknowledged duty of candor in disclosing information that may be relevant to the examination of claims to the present invention. However, it is respectfully submitted that none of the above information discloses, teaches, suggests, shows, or otherwise renders obvious, either singly or when considered in combination, the invention described and claimed herein.

SUMMARY OF THE INVENTION

The present invention provides a planar sensor for sensing lateral displacement and shear force. The planar sensor measures the displacement of a small ferromagnetic or diamagnetic target that is positioned and allowed to move laterally over a series of specially shaped and orientated planar coils. The coils are preferably multi-layer printed circuit boards (PCB) that contain the planar windings and in other embodiments can be fabricated using flexible PCBs or using micro electromechanical (MEMS) assemblies. The target and its assembly is preferentially constrained to a general area using a compliant surround material or using a series of spring elements.

Other novel features which are characteristic of the invention, as to organization and method of operation, together with further objects and advantages thereof will be better understood from the following description considered in connection with the accompanying drawings, in which preferred embodiments of the invention are illustrated by way of example. It is to be expressly understood, however, that the drawings are for illustration and description only and are not intended as a definition of the limits of the invention. The various features of novelty which characterize the invention are pointed out with particularity in the claims annexed to and forming part of this disclosure. The invention resides not in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is neither intended to define the invention of this application, which is measured by the claims, nor is it intended to be limiting as to the scope of the invention in any way.

Certain terminology and derivations thereof may be used in the following description for convenience in reference only, and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted. Further the following description may describe any combination of spring and/or bearing as a suspension mechanism.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Figure 1:
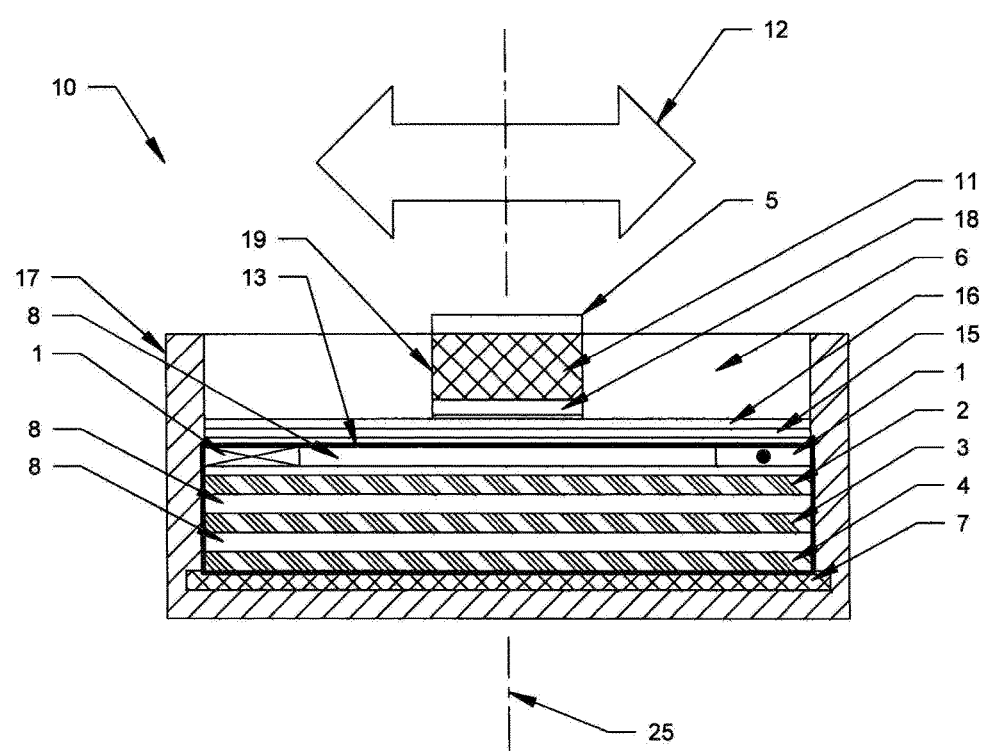
FIG. 1 shows a preferred embodiment of a planar sensor for sensing lateral displacement and shear of this invention.

Referring to FIGS. 1 through 12B, wherein like reference numerals refer to like components in the various views, there is illustrated therein a new and improved planar sensor for sensing lateral displacement and shear.

A preferred embodiment is shown in the sectional view shown in FIG. 1. The planar sensor 10 measures the lateral displacement 12 of a constrained target assembly 19. The target assembly 19 contains a small ferrite, diamagnetic or magnetically permeable target 11 positioned above the number of coils in a coil assembly 13, and constrained with a compliant surround material 6 (for example Poron, thermoplastic, urethane or silicone rubber). In other embodiments of this invention, the compliant surround material 6 may be one or more spring elements attached between the sensor housing 17 and the target assembly 19.

The planar sensor 10 comprises of; at least two or more geometrically shaped and scaled sense coils 2, 3, 4, that are orientated to at least one axis, at least one drive coil 1 and a target assembly 19. Said coils can be fabricated in the same plane or layered in different planes, or combinations thereof. For example, multiple coils can be interleaved or wound as adjacent windings (using insulated wire), or wound and stacked in separate layers (with insulation between layers as is shown in FIG. 1). Thus these coils may be wound and stacked using conventional coil winding techniques, or preferably, fabricated on layers of a multi-layer printed circuit board. Each coil should be electrically insulated from adjacent layers using films, additional layers or wire coatings well known in the art.

Typically, an adjacent object will produce a force on the target assembly 19 that may result in lateral movement of the target 11 with respect to the planar sensor 10 coil assembly 13. A material layer 5 may be preferably placed on one side of the target assembly 19 containing target 11 to beneficially raise the height of the target assembly 19 and to control the coefficient of friction between the target assembly 19 and an adjacent object whose lateral movement 12 is to be sensed by said planar sensor 10. Typically, the adjacent object may be the underside of a foot, hand, or similar body surface where the planar sensor 10 will be required to measure the interface forces and shear between the adjacent object and the planar sensor coil assembly 13 and housing 17. Preferably, material layer 5 should have a high friction, for example, a grip tape such as 3M™ Safety-Walk™ Slip-Resistant Conformable Tapes (3M, St. Paul, Minn.) and be raised approximately 0.2 to 2 mm above the sensor housing 17 and any compliant surround material 6.

In other embodiments of the invention, a backing layer 7, preferably made from highly magnetic permeable material such as MuMetal or Co-NETIC (Magnetic Shield Corporation), may be used to preferentially shape the electromagnetic field and coupling between the drive coil 1, the sense coils 2, 3, 4 and the target 11. Backing layer 7 also beneficially decreases the susceptibility of the coil to stray fields and reduces planar sensor sensitivity to any nearby metal.

An insulator material 8 may be used in the mechanical structure of the coil and/or sensor layers to separate, shape and scale adjacent windings. In other embodiments of this invention, multiple drive coil 1 windings and/or sense coils can be utilized.

In another embodiment of this invention, the planar sensor 10 may be combined with a pressure or force sensor 15. For example a pressure sensitive piezo-resistive ink electrode combination, such as FlexiForce force sensors made by Tekscan (Boston, Mass.). The force sensor 15 can be preferably mounted between the coil assembly 13 and the target assembly 19. In other embodiments, the force sensor can be mounted on the rear side of the planar lateral displacement sensor, for example, on the backing layer 7 or rear of the sensor housing 17. The inclusion of a force sensor 15 allows the lateral displacement, lateral shear force and vertical force to be measured at the same location within a single planar sensor 10. In other embodiments of this invention, the pressure sensing layer may be incorporated within one of the layers of the coil assembly 13, or planar lateral displacement sensor 10.

In general, the contact area between the target assembly 19 and the force sensor 15, or in other embodiments of the invention, between the target assembly 19 and the coil assembly 13, should be a low friction interface. The lower surface of the target assembly 19 should therefore be flat, smooth and made from a material with a low coefficient of friction such as PTFE, plastic, ceramic or similar. In other embodiments of the invention, it is desirable to use a thin layer 16 as a bearing material between the target assembly 19 and the force sensor 15 (or in other embodiments, the coil assembly 13). Suitable bearing materials include PTFE, Corning® Gorilla® Glass, DELRIN® AF blend—Teflon® fiber filled plastic, and similar materials.

The material selection and structural design of the target assembly 19, sensor housing 17, coil assembly 19 and bearing thin layer 16 should withstand the expected weight and loading that may be associated with said adjacent object. Vertical loading on the sensor (i.e. parallel to axis 25) should result in minimal compression or deflection between the target assembly 19, the coil assembly 13 and the backing layer 7. Therefore the separation between the coil assembly 13 (and its associated drive coil 1 and sense coils 2,3 and 4) and the target 11 should preferably remain constant.

Shear stress, is defined as the component of stress coplanar with a material cross section. Shear stress arises from the force vector component parallel to the cross section. Shear stress is defined as force applied divided by the cross sectional area of the deformed material with area parallel to the applied force. In the planar sensor 10, the shear force is therefore the force required to move the target assembly 19 laterally 12 against the restorative force of the compliant surround material 6. The shear force is therefore measured using a combination of coils (coil assembly 13) and circuitry that determine the relative displacement of the target assembly 19 and the shear force is then calculated from a calibration table or from the relationship between force and the known material characteristics of the compliant surround material 6. Thus if the material deforms according to Hooke's law (the force needed to extend or compress a spring by some distance is proportional to that distance) the shear force can be calculated from the measured target lateral displacement and the spring constant.

In other embodiments of this invention, target 11 may be separate from the planar sensor 10. In this case, measurements are only made if the target 11 is brought into close proximity with the planar sensor 10 (specifically the coil assembly 13 and backing layer 7).

Figure 2:
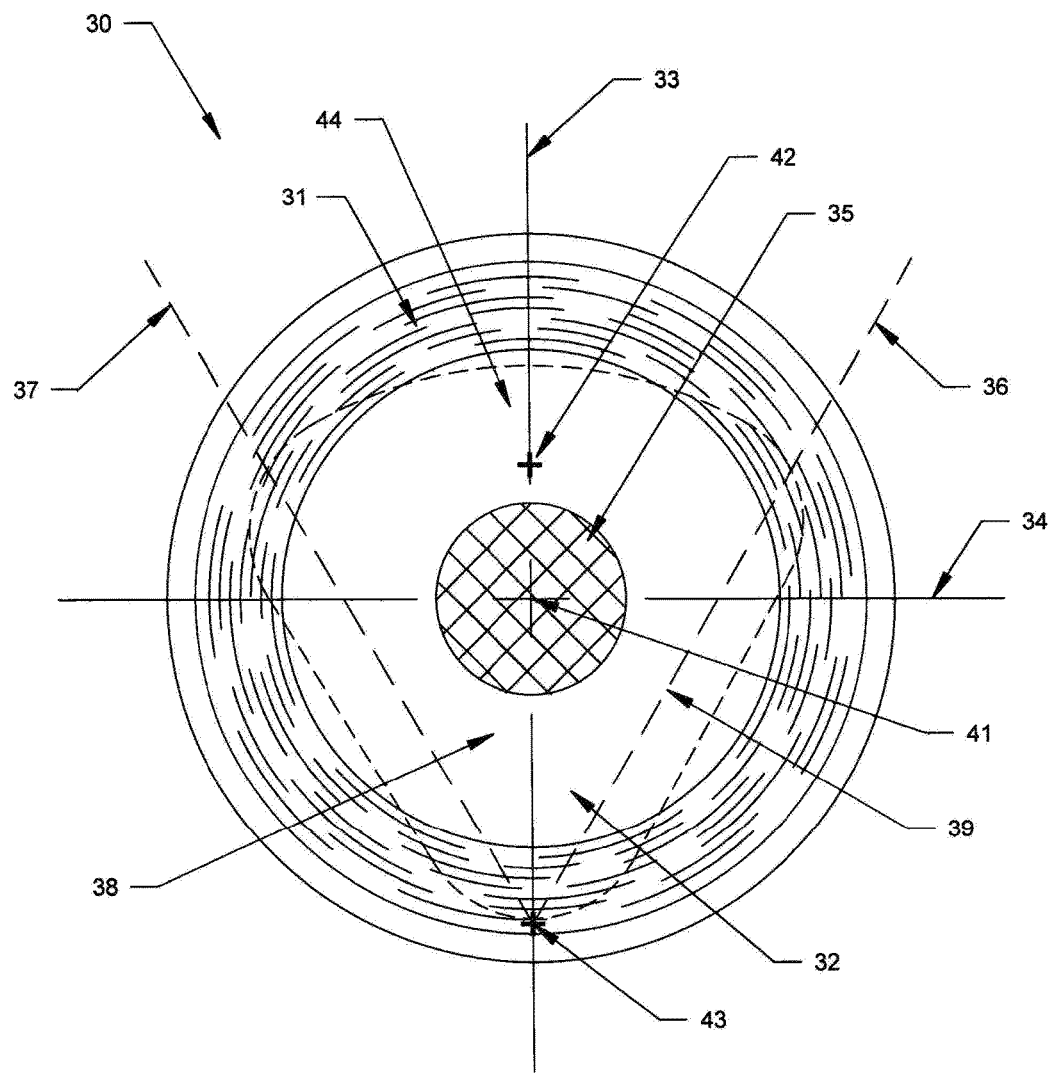
FIG. 2 shows a top down partial view of a planar sensor.

FIG. 2 shows a top down (plan form) view of an embodiment of the planar sensor 30, illustrating various features of the invention. The planar sensor 30 measures the lateral displacement of a target assembly 35. The target assembly 35 should, at its rest or initial zero position, have a center that is located on, or in close proximity to the sensor center point 41. The sensor center point 41 would also typically be on a vertical axis 25, and in planar sensor 30, also correspond to the intersection of horizontal axes 33 and 34. The sensor center point 41 also corresponds to the center of the coil assembly 13. As described hereinbefore, the target assembly contains a small diamagnetic or magnetically permeable material, positioned above a coil assembly, and held in place with a compliant surround material (for example Poron, thermoplastic, urethane or silicone rubber) or spring compliance. The structure of the sensor and the compliant surround material or spring compliance is designed to act to restore the target assembly towards the center point 41.

A planar drive coil 31 partially fills an outer annular section of the sensor. The center portion of said planar sensor 30 contains at least two shaped and scaled sense coils that are positioned in various orientations and in various layers in a coil assembly. By way of example, a single shaped sense coil 39 is shown in FIG. 2.

The drive coil 31 typically comprises of multiple turns and/or windings. In this embodiment, the drive coil 31 has been wound in a circular form. Preferably the coil windings should be planar wound and the diameter of a circular form drive coil 31 should be much greater than the vertical height of the coil winding.

Each of the multiple sense coils in the planar sensor should be orientated with respect to at least one axis, geometrically shaped and scaled (with details described hereinafter) and be primarily located within the center area of the drive coil 31. For example, the sense coil 39 should preferably be constructed such that it has a coil origin 43 that is located on an axis 33, with said axis 33 transecting the drive coil 31. The sense coil 39 should thus also be preferably positioned and shaped (wound) so that it is symmetrical to an axis. In the example shown in FIG. 2, it should therefore be wound to be approximately symmetrical to axis 33. The sense coil 39 may also in certain embodiments of this invention, be wound and positioned such that one side of the sense coil 39 has a smaller cross sectional end form 32 and another side with a larger cross sectional form 44. The shaped and scaled planar windings of the sense coil 39 forms a planar sense area 38. As will be described hereinafter, the planar sense area 38 will contain multiple geometrically shaped graduated windings to control and scale the coupling between the drive coil 31 and each sense coil based on the location of the target assembly 35. Specifically, sense area 38 is designed such that the position of target assembly 35 along axis 33, will translate into a different coupling (between the signal drive coil 31 and said sense coil 39). As will be described hereinafter, the said coupling may be converted into a measurand (i.e. the quantity intended to be measured, for example voltage) related to the position of the target assembly 35. Furthermore, the sense coil 39 geometry and symmetry with respect to axis 33 results in a sensing area 38, such that the position of the target assembly 35 along an axis between the sector limits 36 and 37, produces a measurand that is substantially linear. Thus the position of the target assembly 35 can be determined by sensor electronics that measure said coupling.

Figure 3:
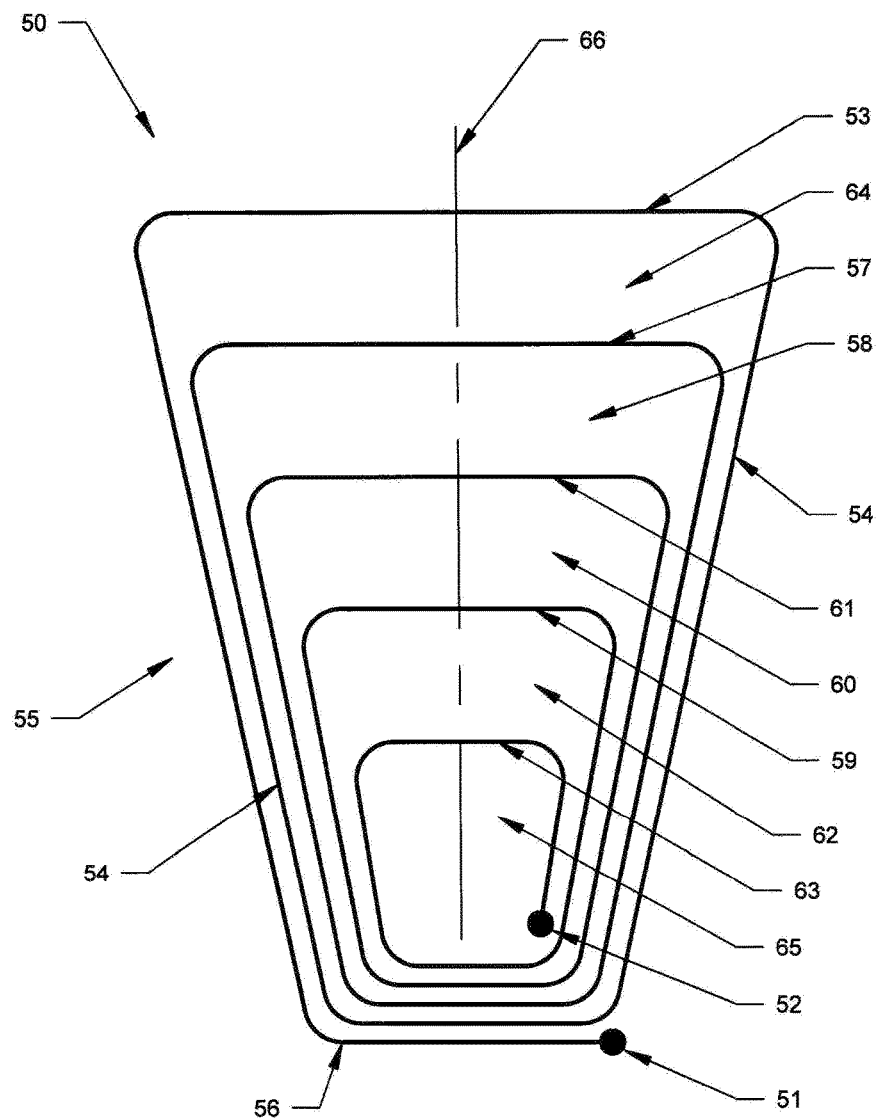
FIG. 3 shows a detailed top down view of a single geometrically shaped graduated sense coil winding.

FIG. 3 shows a detailed top down view 50 of an embodiment of a single geometrically shaped and scaled sense coil winding 55. The sense coil winding 55 has a start 51 and end 52 and is wound with one side with a smaller cross sectional end form 56 and another side with a larger cross sectional form 53. The sense coil winding is wound with a graduated spacing, for example 64, 58, 60, 62 and 65 between each shaped layer. Each winding, for example, 53, 57, 61, 59 and 63 is spaced equally apart and located distal from adjacent windings that are orthogonal to axis 66, but the return windings that are located close to end 56 are tightly arranged (winding should preferably be fabricated adjacent to one another, or as close as the wire winding or PCB track width fabrication limits permit). Similarly the sense coil 55 return windings 54 are tightly arranged (winding should preferably be fabricated adjacent to one another, or as close as the wire winding or PCB track width fabrication limits permit). The sense coil winding 55, aside from the coil start 51 and end 52, is substantially symmetrical with respect to axis 66. A small ferrite, diamagnetic or magnetically permeable target (not shown in this figure), that is positioned at any position along axis 66, between winding 53 and 63, will electromagnetically couple the drive coil (not shown in this figure) to the sense coil winging 55. It can be seen that at any point along axis 66, the coupling of drive coil to sense coil 55 will vary as a function of the lateral position of the target (between winding 63 and 53). As the target moves from winding 63 (upwards in FIG. 3), more sense coil turns (63, 59, 57 and then 53) are be coupled to the sense coil.

FIGS. 4A-4D show detailed planar circuit board layouts for one embodiment of this invention describing details and features of a set of three orientated, shaped and scaled planar sensor windings. These top down, layer views 100, 101, 102 and 103, show by way of example, a planar sensor configuration with one drive coil 105 and three layers of geometrically shaped graduated sense coil windings 108, 138 and 148, that are positioned with various orientations to so as to, in combination, measure the two dimensional lateral displacement of a target (not shown in these views). Each sense coil winding 108, 138 and 148 are similar to the shaped and scaled planar sense coil described in FIG. 3. Each sense coil winding 108, 138 and 148 is positioned on an axis 122, 141, and 149, and each axis is rotated 120 degrees from each other.

Figure 4A:
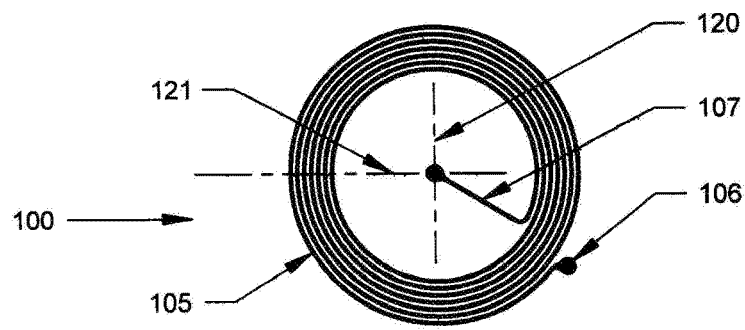
FIGS. 4A-4D show detailed planar layouts for planar sensor windings.

FIG. 4A shows a first view 100 of the drive coil for a planar sensor comprising of a coil 105 with a start 106 and an ending 107. The coil start and/or ending may be connected via inter leading circuit connections (for example PCB via's) to external electronic drive circuitry using techniques that are well known in the art. The drive coil 105 comprises of multiple windings that in this embodiment have been wound in a circular form. Preferably the coil windings should be planar, for example the diameter of the circular form should be much greater than the vertical height of the coil winding. The coil 105 is wound with a center 120 on axis 121.

Figure 4B:
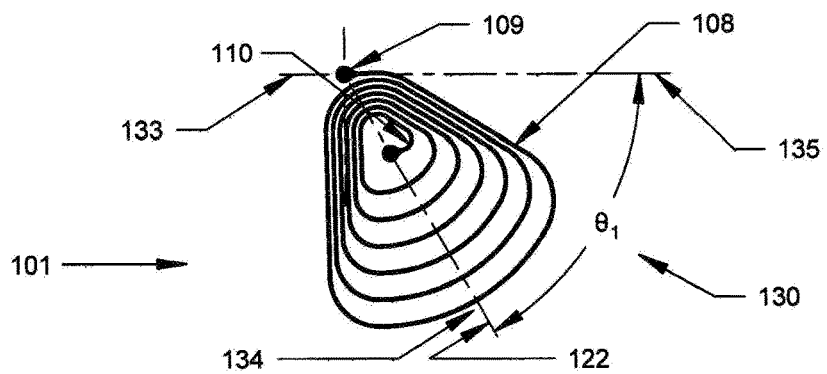

FIG. 4B shows a view 101 of a first planar geometrically shaped graduated sense coil 108. The sense coil 108 comprises of a start 109 at position 133, and end 110, that may be connected via inter leading circuit connections (for example PCB via's) to external electronic receive circuitry using techniques that are well known in the art. The sense coil 108 winding has a number of adjacent coils that are spaced and separated along an axis 122. Thus on axis 122, adjacent windings have a geometric spacing between each turn. Each winding turn, for example, 53, 57, 61, 59 and 63, is thus orthogonal when crossing axis 122, and the planar sense coil 108 is symmetrical to axis 122. Winding turns located close to the distal end 134 of the sense coil 108 are spaced apart away from adjacent windings while turns that are located close to the origin position 133 are wound tightly. In this example, the first sense coil has an axis 122 that is at an angle of $\Theta_1$ 130 from axis 135. Axis 135 is parallel to axis 121.

Figure 4C:
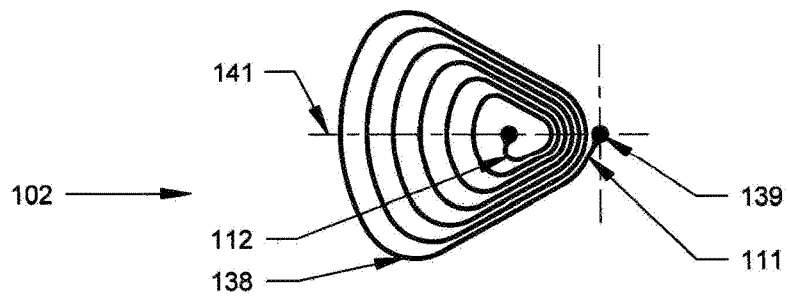

FIG. 4C shows a view 102 of a second planar geometrically shaped graduated sense coil 138. The sense coil 138 comprises of a start 111 at position 139, and end 112, that may be connected via inter leading circuit connections (for example PCB via's) to external electronic receive circuitry using techniques that are well known in the art. The sense coil 138 winding is wound as described hereinbefore and has an axis 141 and is symmetric about this axis. In this example, the second sense coil has an axis 141 that is parallel to axis 135 and axis 121.

Figure 4D:
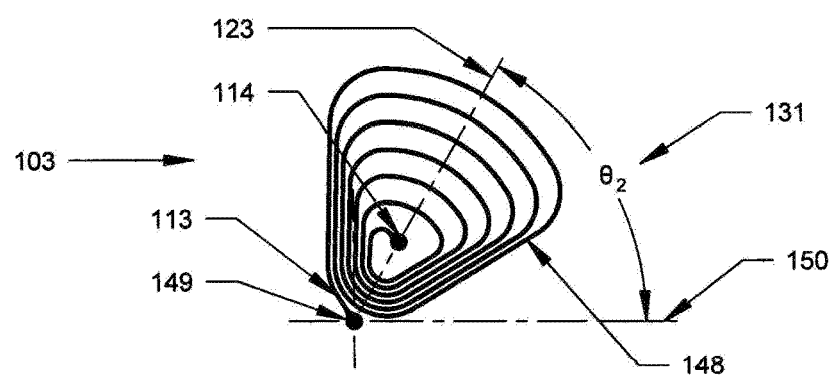

FIG. 4D shows a view 103 of a third planar geometrically shaped graduated sense coil 148. The sense coil 148 comprises of a start 113 at position 149, and end 114, that may be connected via inter leading circuit connections (for example PCB via's) to external electronic receive circuitry using techniques that are well known in the art. The sense coil 148 winding is wound as described hereinbefore and has an axis 123 and is symmetric about this axis. In this example, the third sense coil has an axis 123 that is at an angle of $\Theta_2$ 131 from axis 150. Axis 150 is parallel to axis 121.

FIGS. 4A-4D show an example of three layered and orientated sense coils, 108, 138, and 148. In this example, the sense coil axis 122, 141 and 123, should ideally be spaced 120 degrees from each other. Therefore, three sense coils, $\Theta_1$ 130 and $\Theta_2$ 131 should be 60 degrees. The origin of each of the sense coils 133, 139, and 149 will typically be within the planar area of the drive coil 105. Each of the planar sense coils is positioned so as to cover a zone of interest, over which a target moves and is thus sensed by the combination of the oriented and layered coils. It should also be evident that a minimum of two planar sense coils must be used to determine the position of a target, while three or more sense coils will improve the accuracy and resolution of the measurement.

Figure 5:
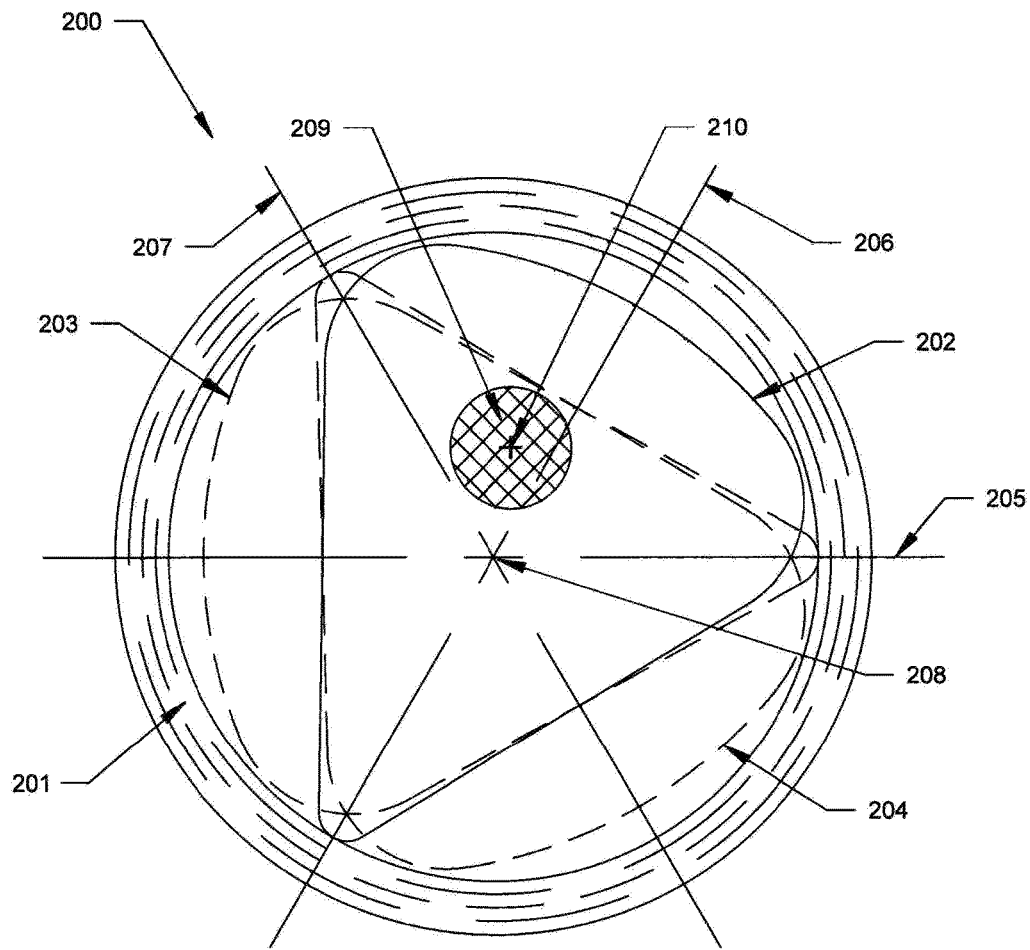
FIG. 5 shows details of a planar sensor for sensing lateral displacement and planar shear.

FIG. 5 shows a top view 200 showing details of one embodiment of a planar sensor for the measurement of lateral displacement in a target and the calculation of planar shear force. The view 200 shows by way of example, the combined positions and orientations of three planar geometrically shaped graduated sense coils 202, 203, and 204 (constructed according to the methods described hereinbefore), a drive coil 201 and a target 209. The view 200 shows a top down combined and orientated view of the coils described in FIG. 4.

Sense coil 202 has an axis of symmetry 206, sense coil 204 has an axis of symmetry 207, and sense coil 203 has an axis of symmetry 205. Each of the sense coil windings in this example fits within the plan-form area of the drive coil 201, and each coil axis is rotated by 120 degrees. As described hereinbefore, the various coils can be layered together, for example using a multi-layer printed circuit board construction or using MEMS fabrication. The three layers of geometrically shaped graduated sense coil windings are orientated so as to, in combination, measure the location 210 of a target 209. The target object 209 is typically a metal, ferrite, diamagnetic or paramagnetic material. As described hereinbefore, as the target moves over the surface of the sensor, the electrical coupling between the drive coil and each of the sense coils changes. Each sense coil 202, 204 and 203, measures the coupling and therefore the position of the target 201 along axis 206, 207 and 205 respectively. Since the sense coils axes are rotated by 120 degrees, the relative target position 210 (in two dimensions) can be calculated by trigonometry and using each sense coils derived target positing (relative to each sense coils axis). Therefore the position of the target within the sensing of the planar sensor can be derived. The sensing area will depend on the size of the target and would typically be contained within the drive coil area.

Figure 6:
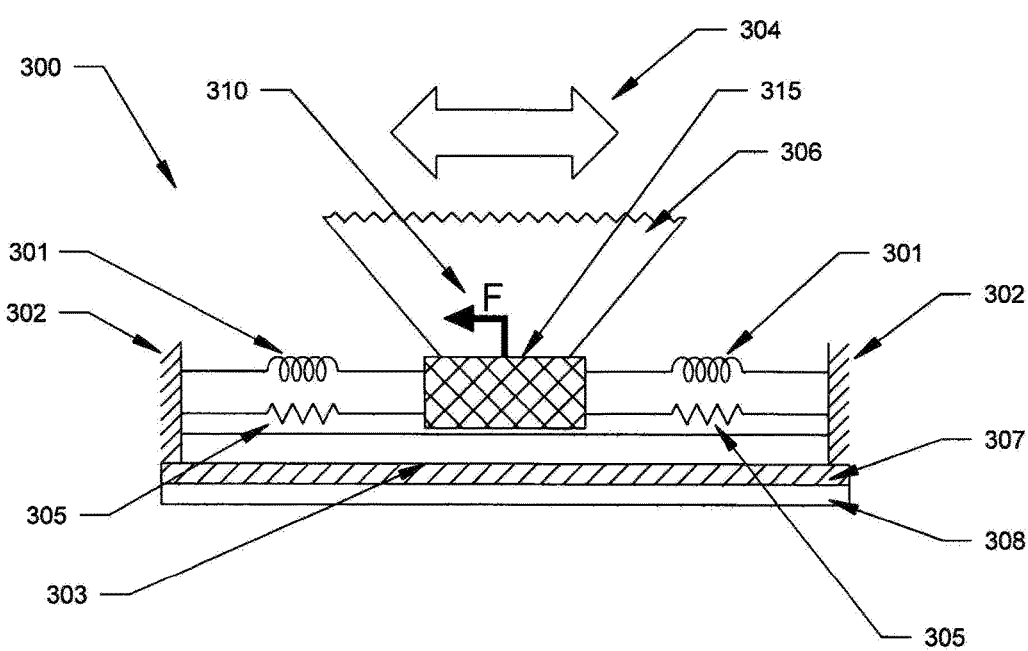
FIG. 6 is a view showing a mechanical equivalent circuit for the planar sensor for sensing lateral displacement and shear.

FIG. 6 is a view 300 showing a view illustrating the mechanical equivalent circuit elements for the planar sensor used for sensing lateral displacement and shear. The planar sensor comprises of the following mechanical elements; a target assembly having a mass 315, a compliant surround material having a mechanical impedance 301 and 305, that is used to constrain the target assembly over the planar layered sensor coil assembly 303, and act on the target assembly. As described hereinbefore, an external adjacent object 306 is in contact with the target assembly mass 315 and couples a lateral, or shear force 310 onto said target assembly mass 315. The coefficient of friction between the external adjacent object 306 and the target assembly mass 315 is designed to be high enough that there is no slip between these items. Thus the lateral (shear) force imparted by the external adjacent object acts directly on the target assembly 315. The coefficient of friction between the target assembly mass 315 and the coil assembly 303 is designed to be very low (using bearing surfaces and specially selected materials as described hereinbefore). The lateral force may result in the lateral displacement 304 of the target assembly mass 315 over the sensor coil assembly 303, if the force is enough to displace the mass of the target assembly mass 315, compress the compliant impedance 301 and overcome the effects of friction and mechanical resistance 305. The compliant impedance 301 is designed to center the target assembly 315 over the windings 303 when no external loading is applied.

Selection of the planar sensor component mass, mechanical impedances and interface conditions is critical for the sensor operation. The target assembly mass 315 should generally be small compared to the overall planar sensor mass. If the planar sensor housing 302 is mounted onto another body, that body mass may dominate and increase the effective sensor housing mass. As described hereinbefore, an additional permeable layer 307 is placed below the sensor coil assembly 303 to increase the electromagnetic coupling between the drive coil winding, the target and each of the sense coils. A suitable material may be a single or number of ferrite slabs such as 3F3, commercially available from Ferroxcube, or a highly permeable material such as MuMetal or Co-NETIC (Magnetic Shield Corporation). Not shown on any of the figures are the insulating layers between each of the coil laminations and the layer of high permeability material 307. The permiable layer 307 thus adds to the sensor housing mass.

The compliant surround impedance 301 and 305 can be typically modeled as a spring (compliance) and resistance (loss). Therefore the surround impedance 301 will be mechanically resonant with the target assembly mass 315 at a frequency f approximately given by:

$$f = \frac{1}{2\pi}\sqrt{\frac{k}{m}}$$

Where k is the compliant surround 301 stiffness, and m is the target assembly mass 315. The compliant surround resistance 305 will damp the resonance and any unforced oscillations of the target assembly mass 315. Therefore some damping is desirable in the sensor system. The planar sensor should be operated well below frequency f, and typical biomechanical application would require the sensor to operate at less than 1 kHz. Therefore the stiffness and damping of the compliant surround can be selected once the upper frequency and target assembly mass 315 are known.

In other embodiments of this invention, a pressure sensing layer 308, for example a pressure sensitive piezo-resistive ink electrode combination, can be mounted on the rear side of the planar lateral displacement sensor. This configuration allows the lateral displacement and vertical force to be measured at the same location.

Figure 7A:
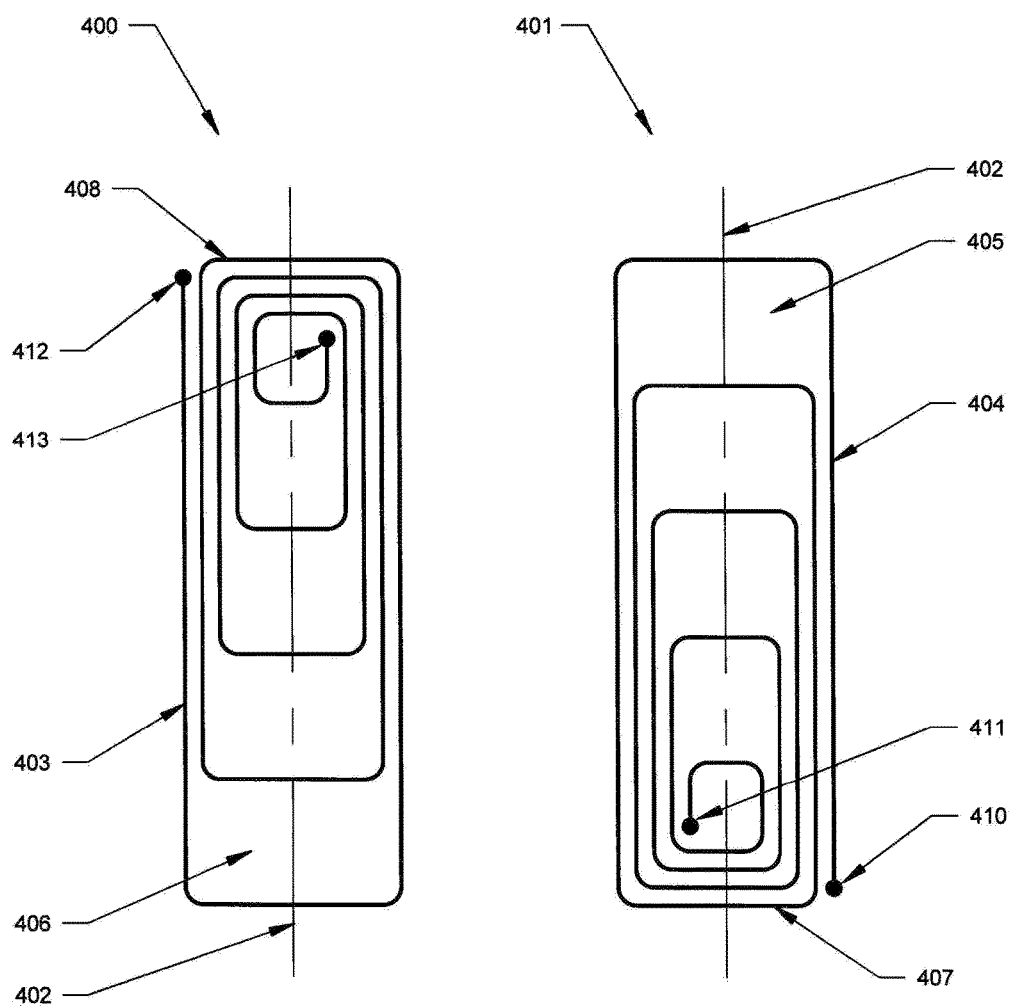
FIG. 7A shows a view that discloses a first planar geometrically shaped and graduated sense coil and a second planar geometrically shaped and graduated sense coil that are both aligned on the same axis of symmetry.

FIG. 7A shows a view 400 that shows a pair of planar geometrically shaped graduated sense coils 403 and 404 that are both aligned on the same axis of symmetry 402. Sense coil 403 has a winding start terminal 413 and end terminal 412, while sense coil 404 has a winding start terminal 411 and end terminal 410. The planar sense coils 403 and 404 are intended to be fabricated as layers with the coils positioned over each other. The end 406 of sense coil 403 is therefore positioned over the start 407 of sense coil 404 and the pair of sense coils is co-planar. Each co-planar coil is therefore wound in opposition to each other.

As described hereinbefore, the position of a target object 209 (typically a metal, ferrite, diamagnetic or paramagnetic material) changes the coupling between a drive coil and the planar sensor sense coils, in this view 400, the coplanar coils 403 and 404. The drive coil is usually excited with an AC voltage that will result in an AC current in the drive coil and sense coils (based on the target position and the coupling between the coils). In a situation where there is a uniformly permeable space surrounding the co-planar windings, the difference between the current induced in each of the co-planar sense coil windings will be zero, as they have the same geometric scaling and area-turns product and are orientated in opposition to each other. However, if the target, which has a different permeability and whose size is small relative to the winding area, is placed in reasonable proximity to the windings along an axis 402, then it will cause a non-uniform coupling of the drive coil and sensor windings fields. Depending on the position of the target, it will cause a difference in the induced currents in the sense coils, and the difference will be larger depending on the distance of the target from the centre of the windings. Therefore the operation of the co-planar coils 403 and 404 in this embodiment of the invention, will be differential. The positioning and orientation of sense coil 404 and sense coil 403 result in windings that scale geometrically in opposite directions.

Figure 7B:
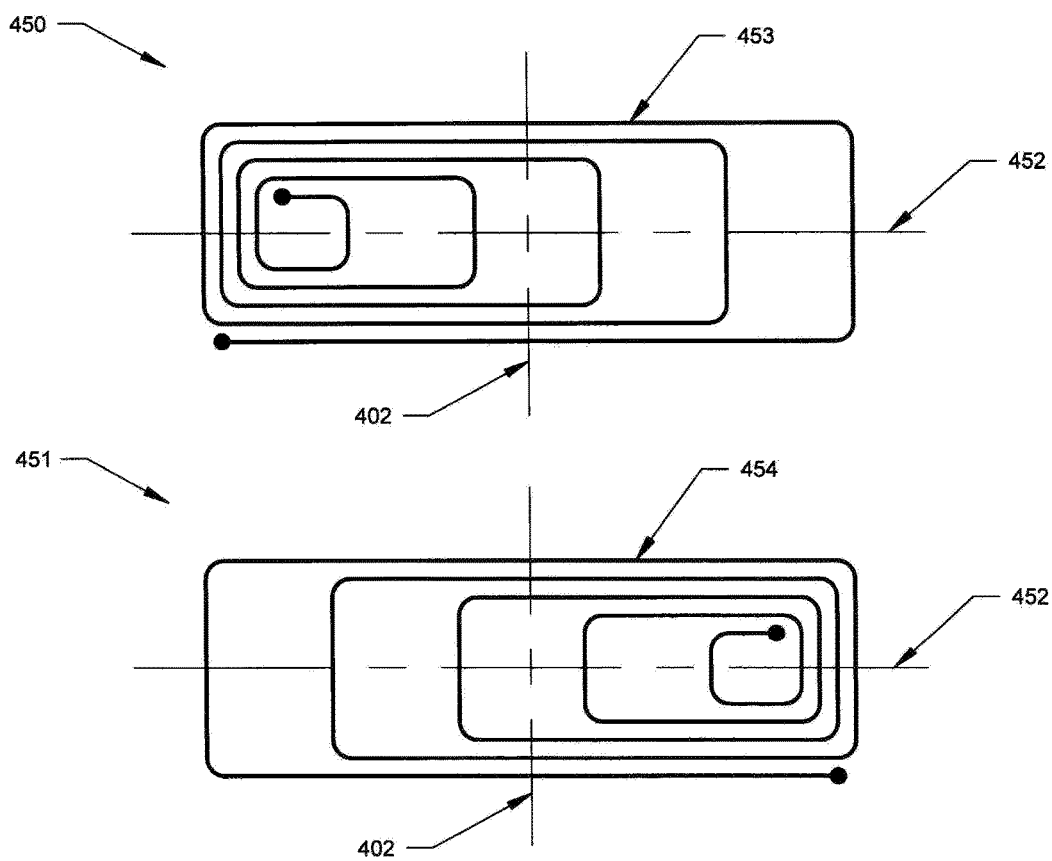
FIG. 7B shows an additional pair of sense coils that are orientated on an orthogonal axis.

Similarly, other embodiments of this invention can use additional pairs of co-planar geometrically shaped graduated sense coil to provide differential measurements of the lateral displacement of a target along axes that are orientated at various angles to axis 402. For example, the view 450 and 451 in FIG. 7B, show an additional pair of sense coils 453 and 454, that are orientated on an axis 452 that is orthogonal to axis 402. The pair of sense coils 453 and 454, are intended to be fabricated as co-planar layers and each coil is therefore wound in opposition to each other. Thus this co-planar sensor pair can be used to differentially measure the lateral displacement of a target along the new axis 452.

Figure 7C:
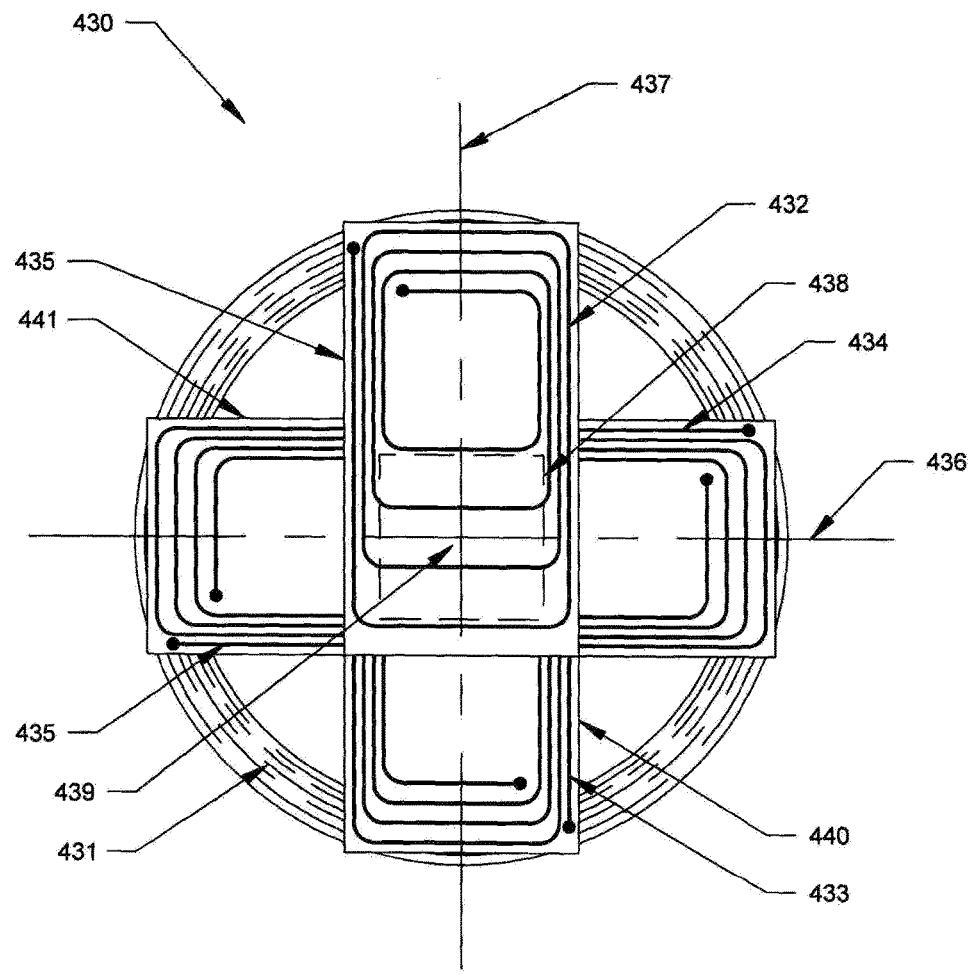
FIG. 7C shows a combined view of two pairs of geometrically shaped and graduated co-planar sense coils that are orthogonally orientated within the planar area of one or more planar drive coils.

FIG. 7C shows a combined view 430 of two pairs of geometrically shaped and graduated co-planar sense coils 440 and 441, that are orthogonally orientated on axes 437 and 436 respectively, within the planar area of one or more planar drive coils 431. Co-planar sense coil 440 comprises of two geometrically shaped graduated sense coil windings 432 and 433. Co-planar sense coil 441 comprises of two geometrically shaped graduated sense coil windings 434 and 435. The co-planar sense coils 440 and 441, and their component geometrically shaped graduated sense coil windings 432,433, 434 and 435, are positioned with interlaced and overlapping windings that result in a mutual sense area 438. The mutual sense area 438 is over the planar sensor center 439 and demarcates the region in which the position of a small ferrite, diamagnetic or magnetically permeable target may be measured.

Combining two pairs of orthogonal co-planar windings will therefore result in the differential measurement of a said targets position along two axes, and the two dimensional position of said target can be directly derived from these measurements. Orthogonal co-planar coil combinations are therefore advantageous as the two dimensional position (or coordinates) of said target can be calculated without the need for any trigonometric scaling. Differential measurements are also much less prone to noise and interference and are therefore preferable for most planar sensor applications.

Figure 8:
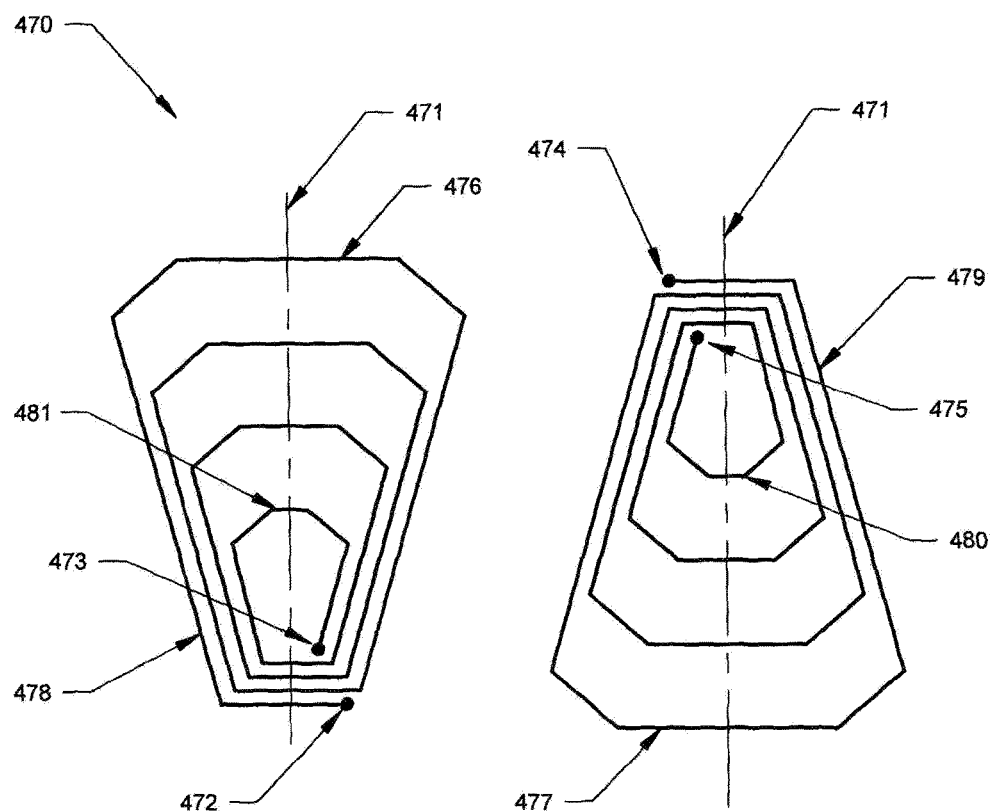
FIG. 8 shows a view that discloses another embodiment that discloses a compact first planar geometrically shaped graduated sense coil and a compact second planar geometrically shaped graduated sense coil that are both aligned on the same axis of symmetry.

FIG. 8 shows a view 470 of another embodiment of this invention, showing another example of compact planar orientated, shaped and scaled sense coils. Two pairs of compact geometrically shaped sense coil windings 478 and 479, are both aligned on the same axis of symmetry 471. Sense coil 478 has a winding start terminal 473 and end terminal 472, while sense coil 479 has a winding start terminal 475, and end terminal 474. As described hereinbefore, the planar sense coils 478 and 479 are intended to be fabricated as layers with the coils positioned over each other. The end winding 476 of sense coil 478 is therefore positioned over the start winding 480 of sense coil 479, and, end winding 477 of sense coil 479 is therefore positioned over the start winding 481 of sense coil 478. Thus the pair of sense coils 478 and 479 are co-planar. The positioning of sense coil 478 and sense coil 479 therefore result in windings that scale geometrically in opposite directions. Therefore the output from each of the sense coils is differential and this can (with appropriate electronics) produce higher sensor sensitivity to lateral target movement along axis 471.

This embodiment also shows compact planar orientated, shaped and scaled sense coils 478 and 479, with shaped windings (for example 476, 481 and 477, 480 respectively). Specifically, the end of each geometrically shaped coil winding is symmetrically tapered on either side of axis 471. There are several advantages for doing this; firstly the compact planar sense coils can optimally fit within a circular drive coil and, the active areas of each of the co-planar sense coils are aligned. The active linear area of sense coil 478 is between winding 481 and 476 and the active linear area of sense coil 479 is between winding 480 and 477. Generally the coupling is non-linear in close proximity to the closely spaced windings in a region close to the start of the coils (i.e. the area near winding start terminal 473 for sense coil 478, and winding start terminal 475 for sense coil 479).

Similarly, combining two pairs of compact planar orientated, shaped and scaled co-planar sense coils on orthogonal axes will result in a sensor for the differential measurement of target two dimensional position. Further, the two dimensional position of said target can be directly derived from the measurements of coupling associated with each orthogonal co-planar sense coil (without the need for any trigonometry calculations). Differential measurements are also much less prone to noise and interference and are therefore preferable for most shear sensing applications.

Figure 9A:
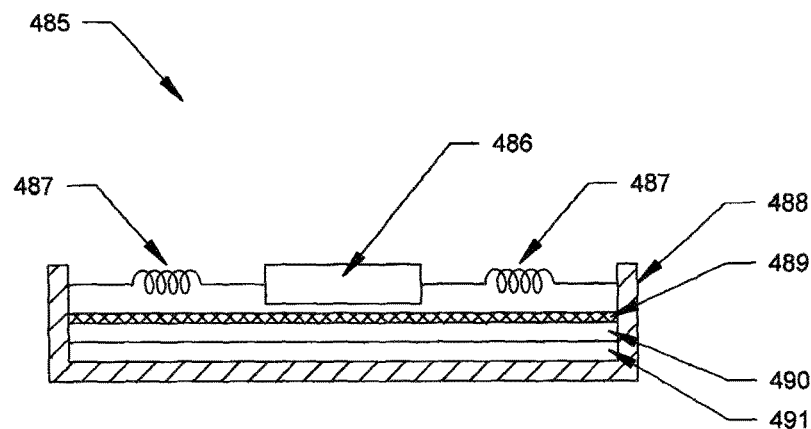
FIG. 9A-9B show a side and top view of preferred embodiments of a planar lateral displacement sensor utilizing multiple spring elements to constrain the target.
Figure 9B:
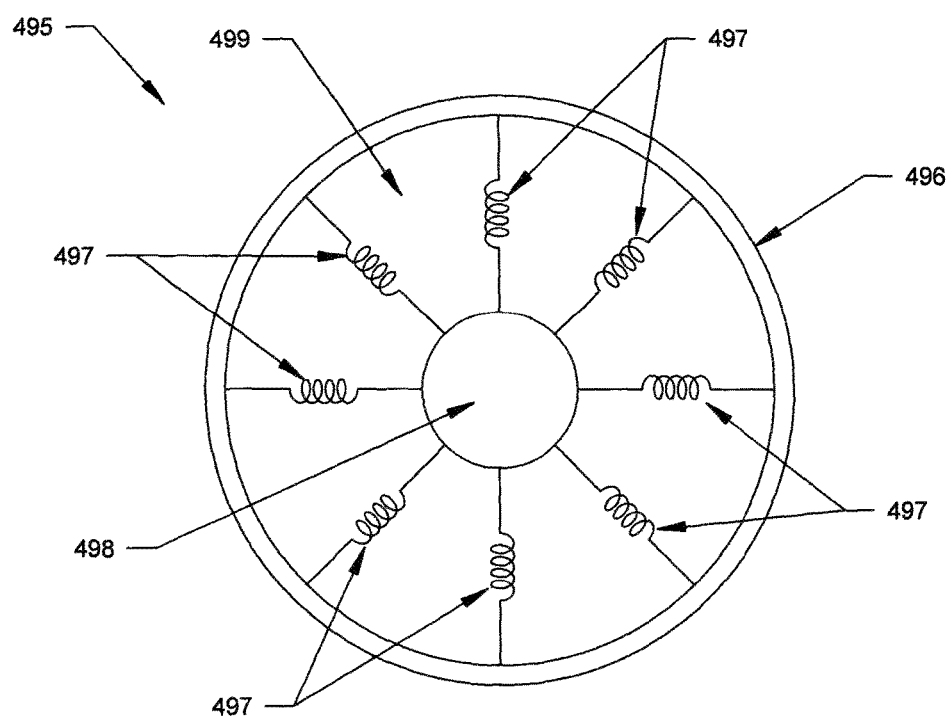

FIGS. 9A and 9B show an alternate embodiment of the planar sensor. FIG. 9A shows a side view 485 of the planar sensor comprising of a target assembly 486, a sensor housing 488, bearing layer 489 (and in some embodiments a pressure sensor), coil assembly layer 490, backing layer 491 and mechanical spring elements 487. The mechanical spring elements 487 may be discrete spring suspension elements. In some embodiments, spring suspension elements 487 may be constructed using an elastomeric material, for example silicone rubber, or thermoset rubber polymer and the like. In certain embodiments it is preferable to pre-stretch the elastomeric suspension element 487 to hold it in tension—this may be accomplished by manufacturing the elastomeric suspension element 487 with a shorter length than the distance from the housing wall 488 to the target assembly 486, thereby stretching the suspension element during assembly, and providing an initial preload to the target assembly. Suspension 487 elements may in some embodiments protrude through the housing wall 488, having a thicker portion, or plug, exterior to the housing 488, thereby acting as an attachment point.

FIG. 9B shows a top view 495 of the planar sensor comprising of a target assembly 498, a sensor housing 496, coil assembly layer (or in some embodiments, bearing layer) 499, and multiple mechanical spring suspension elements 487. The multiple mechanical spring suspension elements 497 are located between the target assembly 498 and planar sensor housing 496. The number and location of spring suspension elements 487 is chosen as a compromise between linearity, form factor and the required suspension compliance or stiffness.

FIG. 9A-B also show a preferred embodiment for the mechanical spring suspension or compliant surround material for the planar sensor. This embodiment will beneficially reduce sensor hysteresis as the spring suspension elements 497 (and 487) are springs that act in combination. For example, in FIG. 9A, the action of an adjacent object may cause the lateral movement of the target assembly 486 resulting in the compression and expansion of the spring elements 487. Once the external object is released (i.e. no shear force on the sensor), the target assembly will be returned to its start position under the action of the said springs. The recovery of bulk compliant materials (such as poron rubber) during expansion is relatively slow as the material recovers in a viscous manner—this produces significant planar sensor hysteresis (on the order of several seconds). In contrast, springs and compliant suspension elements that are attached and act in compression and tension can recover much more rapidly. Therefore hysteresis in this embodiment, may be reduced to less than 100 ms and the planar sensor is capable of accurately measuring the dynamics associated with shear force.

Figure 10:
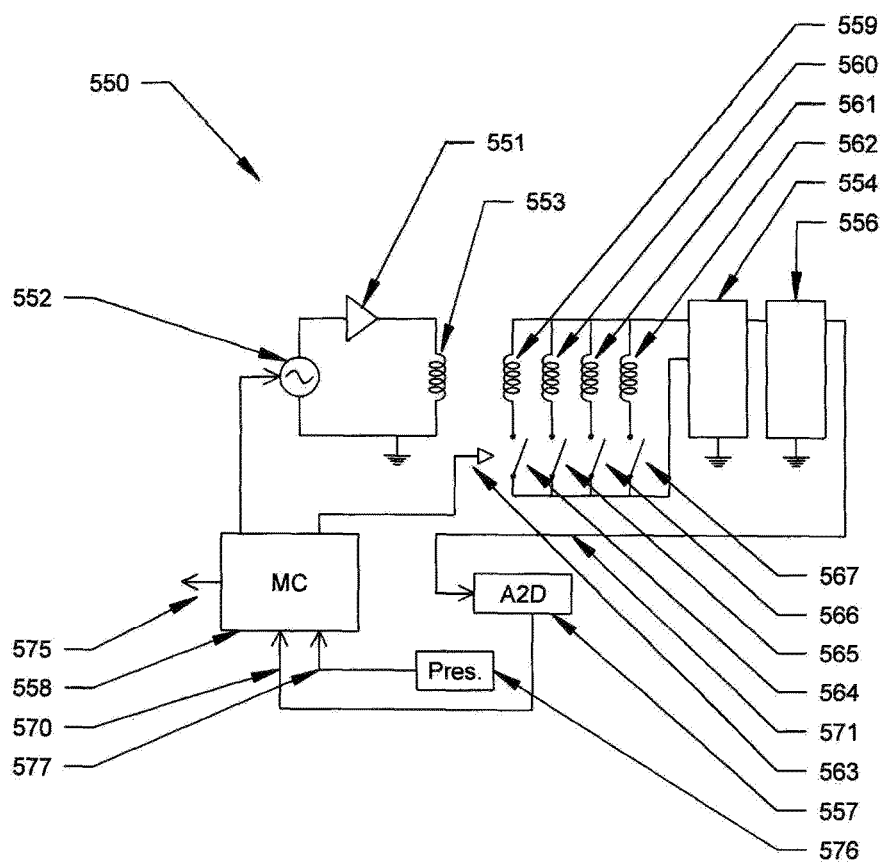
FIG. 10 shows a view of a block diagram describing an exemplary sense circuit or electronic means for exciting said one or more drive coils measuring the response on one or more sense coils and a means for calculating the displacement and shear force from a planar sensor.

FIG. 10 shows a view 550 of a block diagram for an exemplary circuit or electronic means for exciting one or more said drive coils, measuring the response on one or more said sense coils, and, a means for calculating the displacement and shear force from said planar sensor. As described hereinbefore, if a target object, which has a different permeability and whose size is small relative to the winding area, is placed in reasonable proximity to the windings, then it will cause a non-uniform coupling of the drive and sense coil fields. Depending on the position of the object, it will cause a difference in the induced currents in the sense coil, and the difference will be larger depending on the distance of the object from the centre of the windings.

The exemplary circuit 550 comprises of an oscillator 552 that may be synchronized with a microprocessor controller 558, driving an optional drive coil amplifier 551, and one or more said drive coils 553. The drive coil winding is typically excited using a reasonably high-frequency AC drive, and the resulting drive current can induce a current in each of the sense coil windings. For example, the drive coil can be driven by a sinusoidal oscillation frequency that is usually chosen to be in the range 2 kHz to 20 MHz. By way of example, drive coil 553 would induce a current in sense coil windings 559, 560, 561 and 562 when each controllable switch 564, 565, 566 and 567 are closed. Each controllable switch, 564, 565, 566 and 567, can be addressed 563 and selected by the microprocessor controller 558. Generally, each sense coil is selected in sequence and additional circuitry 554, 556 and 557 is used to measure and record the response of the selected (or connected) sense coil.

Synchronous detection can be used to detect the induced current signal in each of the sense coils with a high signal-to-noise ratio. By way of example, 554 would be a synchronous detector circuit and block 556 would then typically be a low pass filter for extracting the modulated coupled target measurement signal. In other examples, a dedicated inductive sensor such as the Microchip mTouch inductive touch sense chip can be used to scan and measure each sensor coil.

Generally the output 571 of the detection circuit component circuitry 554 and 556, would result in a voltage signal that is proportional to the coupling between the drive coil and selected sense coil. An analogue to digital converter 557 may be used to convert said voltage signals into digital data 570, and a microprocessor controller 558 can be used to store and compare each of the selected and sequenced sense coil measurement values. If the sense coils pairs are wound differentially, they can be combined such that the sense coil currents are summed directly, or preferably, the differential pairs can be measured separately and their outputs subtracted electronically or using mathematical manipulation in the microprocessor controller 558. The microprocessor controller 558 may also be used to store and use the results of sensor calibrations to improve sensor accuracy.

The microprocessor controller 558 determines the position of said target by calculating the coupling and voltage signals from one or more drive coils and the known orientations of one or more shaped and scaled planar wound sense coils. The microprocessor controller 558 can output 575 this measurement to another device such as a computer, smart phone or data collection device using standard interfaces such as USB, I2C, Bluetooth, WiFi, Zigbee, CAN bus, SPI, serial, parallel and similar.

In some embodiments of this invention, pressure sensor readings may also be detected and processed using circuitry 567 well known in the art. The pressure data 577 can also be stored and transmitted, or used by the microprocessor controller 558 to scale the calculated coupling and target displacement (or shear force) based on the measured loading (pressure) and a previous sensor calibration. This approach allows the system to compensate for the potential practical effects of friction in the measurement of shear.

A method for determining a calibration for a planar sensor would be to measure a known lateral load at various simultaneous vertical or force loads and use this in a look-up table on said microprocessor controller. Such a calibration would include the steps of placing the planar sensor on a known (calibrated) reference load cell that can measure vertical and horizontal loading, providing a lateral or horizontal force on the planar sensor (for example by attaching a lightweight cable onto the target assembly, running the cable over a pulley and adding weights, and simultaneously adding a vertical load onto the planar sensor (for example using a pneumatic piston or press). Multiple measurements at different vertical and lateral loads would them be made using the planar sensor and these would be compared to the reference load cell sensor.

Figure 11:
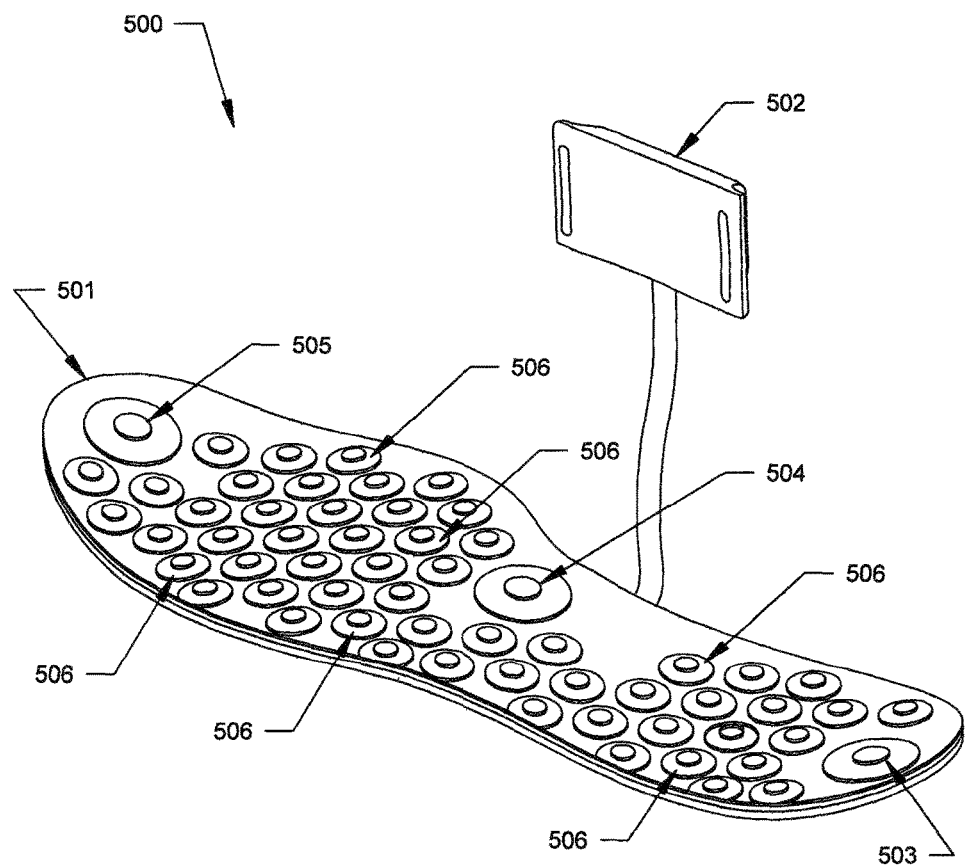
FIG. 11 shows a view of an instrumented insole for a shoe.

FIG. 11 shows a view 500 of an instrumented insole 501 intended for use within a shoe. The instrumented insole 501 contains an array of force or pressure sensors 506 together with multiple planar lateral displacement sensors 503, 504 and 505. The instrumented insole has a battery and electronic circuitry 502 for the collection of sensor data and storage, and may transmit this data in real time to various displays, for example a smart phone or computer. The instrumented insole 501 therefore provides a means for measuring the instantaneous pressure over the undersurface of a foot together with the shear loading at one or more locations under the foot.

In other embodiments of this invention the electronics 502 may be located within the insole. Further embodiments of this invention may include electronics 502 that includes an inertial sensor (INS) that can track the acceleration, angular velocity and position of the instrumented foot sole. The INS data can be combined together with the pressure (center of pressure) and shear data to provide an accurate biomechanical measure of the state and orientation of the foot and user.

Figure 12A:
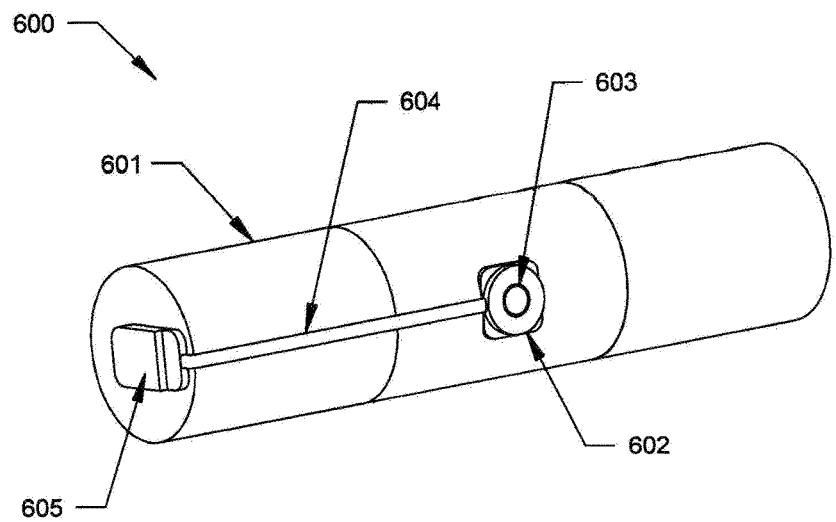
FIGS. 12A-12B show other embodiments of planar lateral displacement sensors imbedded in a various objects.
Figure 12B:
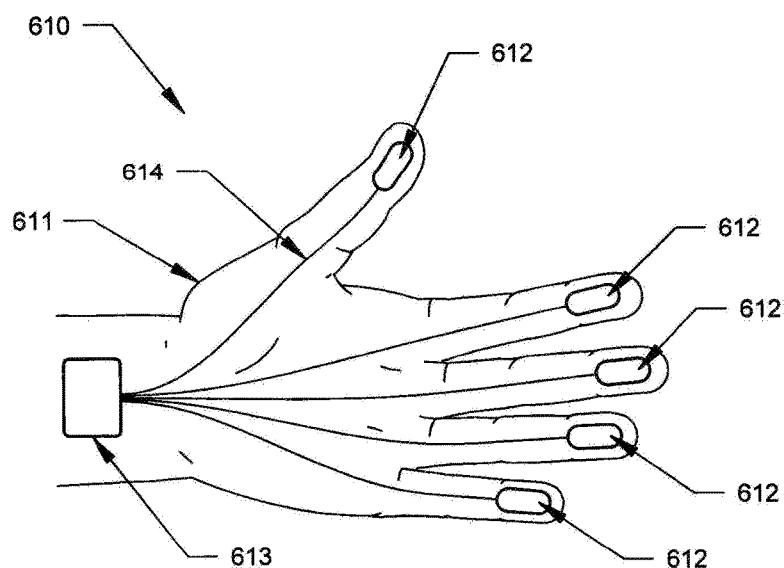

FIGS. 12A-12B show planar lateral displacement sensors imbedded in a various objects. By way of example, FIG. 12A shows a view 600 of a handle 601, for example the handle of tennis racket, in which a planar lateral displacement sensor 602 is mounted. A target 603 is designed to be in contact with part of the hand (for example the palm) of a user who is grasping said handle 601. Wiring 604 connects the sensor to electronics 605. Typical applications of this embodiment may measure a user's finger grip pressure and shear during activities where the user is grasping said handle 601 and coving said sensor 602. In other embodiments of this invention, target 603 may be separate from the planar sensor 602. In this case, measurements are only made if the target 603 is brought into close proximity with the planar sensor 602 (in this case comprising of the assembly, compliant surround, backing layer and housing).

FIG. 12B shows another practical application with a view 610 of a glove 611 in which various planar displacement sensors 612 have been mounted. Wires 614 connect the sensors to electronics 613. Typical applications of this embodiment may measure a user's finger grip pressure and shear during activities where the user is grasping objects while wearing said glove 612 containing one or more of said sensors 612. In other embodiments of this invention, the sensor target, or target assembly may be separate from the planar sensor 612. In this case, measurements are only made if the target is brought into close proximity with the planar sensor 612.

Embodiments of the planar sensor for sensing lateral displacement and shear comprise of the following components; a planar sensor made up of one or more planar drive coils, one or more shaped planar sense coils placed in proximity to said drive coils, a target material that is placed within the sensing area of said coils, a means for supporting said target that holds said target a fixed distance from the coils and allows said target to move laterally, a magnetically permeable base layer, an electronic means for exciting drive coil and measuring the response on one or more sense coils, a means for calculating the displacement and shear force placed on said target, and a means for coupling said target onto a body. Preferred embodiments include planar sensors that are constructed using at least three geometrically shaped, stepped and interlaced sense circuit windings, and at least one primarily circular drive coils. Exemplary planar sensor designs may be constructed using multi-layer printed circuit board (PCB) or flexible circuit construction techniques, where a common ground between drive and sense coil circuitry may be used to reduce number of layers.

In other embodiments of this invention a pressure or force sensor can be included within the planar shear sensor layers in order to measure any loads that are orthogonal to the planar sensor lateral displacement. This configuration is suitable for use in biomechanical shear and pressure mapping; for example, it can be mounted within the insole of a shoe and used to measure the foot pressure distribution, center of pressure and together with shear, used to determine the ground reaction force of a foot when in contact with the ground. In other embodiments, it is desirable to include an inertial sensor (containing at least one multi axis accelerometer and rate gyrometer) in order to track the kinematics of the limb especially during the periods that the shoe is not in contact with the ground.

In yet another embodiment of this invention, the target may be mounted in one layer of material and the drive and sense coils in another layer of material, and the layers may be laminated or joined together in some manner to make a make a multilayer structure. For example, the target may be mounted in the insole of a shoe and the drive and sense coils may be mounted in the fixed sole of the shoe; or the target may be mounted in the shell (outer layer) of a glove and the drive and sense coils may be mounted in the lining of the glove which is attached to the inside of the glove.

Accordingly, one embodiment of the present invention may be characterized as a sensor for sensing lateral displacement and shear including a sensor housing; one or more planar drive coils in the housing; one or more shaped planar sense coils within a planar area of the drive coils; a target held in a suspension a fixed distance from the planar drive coils and the sense coils; a magnetically permeable base layer; electronic means for exciting the drive coils and measuring the response on the sense coils; and means for calculating the displacement and shear force of the target and the sense coils.

Another embodiment of the present invention may be characterized as a sensor for measuring lateral displacement and shear between two surfaces, including one or more planar drive coils and one or more shaped planar sense coils attached to a first surface; a target attached to a second surface; electronic means for exciting the drive coils and measuring the response on the sense coils; and means for calculating the displacement and shear force of the target and the sense coils.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like. Therefore, the above description and illustrations should not be construed as limiting the scope of the invention, which is defined by the appended claims.

What is claimed as invention is:

1. A sensor for sensing lateral displacement and shear, said sensor comprising:
 a sensor housing;
 one or more planar drive coils in said housing;
 at least two geometrically shaped and graduated planar sense coils within a planar area of said one or more planar drive coils, each planar sense coil defining a separate plane, wherein said separate planes are stacked, adjacent and parallel;
 a target held in a suspension a fixed distance from said one or more planar drive coils and said planar sense coils, said target forming a part of a magnetically coupled circuit with said one or more planar drive coils and said planar sense coils;

a magnetically permeable base layer;

electronic means for exciting said one or more planar drive coils and measuring a response on said planar sense coils; and means for calculating the displacement and shear force of said target and said planar sense coils.

2. The sensor of claim 1 wherein said planar sense coils comprise differential windings.

3. The sensor of claim 1 wherein said planar sense coils comprise scaled planar windings.

4. The sensor of claim 1 wherein said planar sense coils comprise a plurality of geometrically shaped and graduated sense coils having axes of symmetry positioned with various orientations.

5. The sensor of claim 1 wherein said planar sense coils comprise a plurality of geometrically shaped and graduated sense coils having aligned axes of symmetry.

6. The sensor of claim 1 wherein said planar sense coils comprise coils having axes of symmetry and said coils are interlaced, shaped, aligned and orientated with respect to at least one axis of symmetry.

7. The sensor of claim 1 wherein said planar sense coils are constructed as multilayer printed circuit boards or flexible printed circuit boards.

8. The sensor of claim 1 further including a pressure sensor.

9. The sensor of claim 1 further including an inertial sensor.

10. The sensor of claim 1 including means for calibration and error correction for compensating for the effect of weight.

11. The sensor of claim 1 wherein said housing includes a suspension for reducing hysteresis.

12. The sensor of claim 11 wherein said suspension comprises a spring.

13. The sensor of claim 1 wherein said target includes a high friction material layer to contact an adjacent object.

14. The sensor of claim 1 wherein said target includes a flat lower surface of low coefficient of friction material.

15. The sensor of claim 1 wherein said target comprises a diamagnetic of magnetically permeable material positioned above said one or more planar drive coils and said planar sense coils.

16. The sensor of claim 1 wherein said means for calculating the displacement and shear force of said target and said planar sense coils comprises a processor.

17. The sensor of claim 1 including a backing layer of highly magnetic permeable material.

18. The sensor of claim 1 wherein said sensor is incorporated into a shoe insole.

19. A sensor for measuring lateral displacement and shear between two surfaces, said sensor comprising:

one or more planar drive coils and at least two geometrically shaped and graduated planar sense coils attached to a first surface, each planar sense coil defining a separate plane with an orientation, wherein said separate planes are stacked, adjacent and parallel, and each planar sense coil has a winding origin position and a distal end, and an orientation along which said winding turns proximate the distal end have a different spacing than winding turns proximate the winding origin position;

a target attached to a second surface;

electronic means for exciting said one or more drive coils and measuring a response on said planar sense coils; and means for calculating the displacement and shear force of said target and said planar sense coils.

20. A sensor for measuring lateral displacement and shear between two surfaces, said sensor comprising:

one or more planar drive coils and at least two geometrically shaped and graduated planar sense coils attached to a first surface, each planar sense coil defining a separate plane with an orientation, wherein said separate planes are stacked, adjacent and parallel, and each planar sense coil having a geometrically shaped winding having an origin position and a distal end, and an orientation wherein the winding turns have a different geometric spacing proximate the origin position than proximate the distal end;

a target attached to a second surface;

electronic means for exciting said one or more drive coils and measuring a response on said planar sense coils; and means for calculating the displacement and shear force of said target and said sense coils.

* * * * *

UNITED STATES PATENT AND TRADEMARK OFFICE
CERTIFICATE OF CORRECTION

Page 1 of 1

PATENT NO. : 10,175,125 B1
APPLICATION NO. : 15/019470
DATED : January 8, 2019
INVENTOR(S) : Bruce J. P. Mortimer and Gary A. Zets It is certified that error appears in the above-identified patent and that said Letters Patent is hereby corrected as shown below:

In the Specification

Column 1, Lines 15-17, under STATEMENT REGARDING FEDERALLY SPONSORED RESEARCH OR DEVELOPMENT, replace with the following paragraph:
-- This invention was made with government support under contract number W81XWH-13-C-0129 awarded by the US Army Medical Research & Development Command. The government has certain rights in the invention. --

Signed and Sealed this
First Day of June, 2021

Drew Hirshfeld
*Performing the Functions and Duties of the*
*Under Secretary of Commerce for Intellectual Property and*
*Director of the United States Patent and Trademark Office*